United States Patent
Cook et al.

(10) Patent No.: US 6,511,934 B1
(45) Date of Patent: Jan. 28, 2003

(54) TRANSITION METAL PRECURSORS CONTAINING SULFUR LIGANDS, AND POLYOLEFIN PRODUCTION PROCESSES USING THEM

(75) Inventors: Jessica Ann Cook, Clinton, NJ (US); John Joseph Bielak, South Amboy, NJ (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 126 days.

(21) Appl. No.: 09/690,399

(22) Filed: Oct. 17, 2000

(51) Int. Cl.⁷ ............................... C08F 4/44; C08F 4/70
(52) U.S. Cl. .................. 502/104; 502/103; 502/117; 502/155; 502/168; 502/216; 502/219; 502/220; 502/222; 502/223; 526/161; 526/172
(58) Field of Search ................................. 502/155, 117, 502/222, 223, 219, 220, 103, 104, 168, 216; 526/161, 172

(56) References Cited

U.S. PATENT DOCUMENTS 5,714,556 A * 2/1998 Johnson et al. ............. 526/135

OTHER PUBLICATIONS

Johnson, L.K., et al., "Copolymerization of Ethylene and Propylene with Functionalized Vinyl Monomers by Palladium (ii) Catalysts", J. Am. Chem. Soc. 1996, 118, 267–268.

Johnson, L.K., et al., "New Pd(II)– and Ni(II)–Based Catalysts for Polymerization of Ethylene and α–Olefins", J. Am. Chem. Soc. 1995, 117, 6414–6415.

* cited by examiner

*Primary Examiner*—David W. Wu
*Assistant Examiner*—R. Rabago

(57) ABSTRACT

A catalyst composition for the polymerization of olefins is provided, comprising a transition metal precursor containing sulfur ligands and an activating co-catalyst.

16 Claims, No Drawings

TRANSITION METAL PRECURSORS CONTAINING SULFUR LIGANDS, AND POLYOLEFIN PRODUCTION PROCESSES USING THEM

FIELD OF THE INVENTION

The invention relates to a family of novel catalyst precursor compounds and compositions for the polymerization of olefins, including homopolymers of ethylene, propylene and other alpha-olefins and/or alpha olefin-dienes, as well as copolymers of alpha olefins, cyclic olefins and/or alpha olefin-dienes. In particular, the present invention provides catalyst precursor compounds and catalyst compositions which have good resistance to catalyst poisons, which can provide acceptable activity without the use of more expensive co-catalysts such as methyl alumoxane (MAO) or modified methyl alumoxane (MMAO), and which offer the possibility of polar comonomer incorporation into growing polymer chains.

BACKGROUND OF THE INVENTION

Numerous catalyst precursor compounds have been developed for use in forming catalyst compositions for polymerization of olefins to produce polyolefins. For example, a number of late transition metal complexes have been known to be effective as catalysts, e.g., for oligomerization of ethylene. Brookhart et al. have disclosed that late metals such as Ni, Pd, Fe and Co, when constrained in an appropriate ligand environment, are effective catalysts for the polymerization of ethylene (see e.g., *J. Am. Chem. Soc.* 1996, 118, 267–268 and *J. Am. Chem. Soc.* 1995, 117, 6414–6415). According to Brookhart et al, the ability of the late metal Ni and Pd catalysts to polymerize rather than oligomerize ethylene is due to the steric bulk of the ligand, which prevents olefin approach at the axial sites, thus avoiding chain transfer to olefin. Brookhart et al. assert that the potential advantages offered by these catalysts include the incorporation of functionalized comonomers and the use of less expensive co-catalysts, i.e., diethyl aluminum chloride.

Despite these and other efforts, there remains an ongoing need for catalyst precursor compounds and compositions which enable various olefin polymerization reactions to be performed more efficiently, e.g., at a lower cost with acceptable yield and activity. There is also an ongoing need for such catalyst precursor compounds which offer the possibility of polar comonomer incorporation into growing polymer chains. The catalyst compounds of the present invention, as well as catalyst compositions which contain the catalyst compounds of the present invention, and olefin polymerization reactions which employ the catalyst compounds of the present invention, as described below, satisfy these needs. The present invention provides a family of catalysts which are robust late transition metal complexes containing bulky, neutral, sulfur-containing ligands.

SUMMARY OF THE INVENTION

The present invention provides catalyst precursor compounds for use in olefin polymerization reactions. According to the present invention, there are provided sterically bulky bidentate and tridentate, neutral sulfur-containing ligands, and transition metal complexes of such ligands. The ligands of the present invention contain at least two neutral sulfur-containing linkages. In addition to coordinating to two (and in some cases three) sulfur-containing ligands, the metal centers are also coordinated to two monoanionic groups, e.g., chlorides or methyls.

The catalyst precursor compounds of the present invention, when used in polymerization of olefins, provide acceptable activity and other properties.

The catalyst precursor compounds of the present invention include those having a formula selected from among:

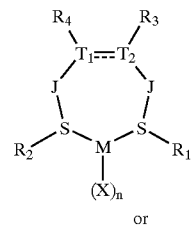

Formula 1 or

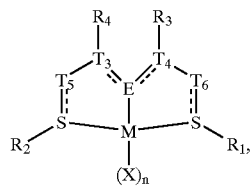

Formula 2 wherein:

E is O, S, N or P;

M is a transition metal;

$R_1$ and $R_2$ are each independently selected from among halogen, alkoxide, aryloxide, amide, phosphide, hydride, hydrocarbyl, substituted hydrocarbyl, halocarbyl, substituted halocarbyl, hydrocarbyl-substituted organometalloid, or halocarbyl-substituted organometalloid, or $R_1$ and $R_2$ are joined to form a ring structure;

$R_3$ and $R_4$ are each independently selected from among hydrogen, halogen, alkoxide, aryloxide, amide, phosphide, hydride, hydrocarbyl, substituted hydrocarbyl, halocarbyl, substituted halocarbyl, hydrocarbyl-substituted organometalloid, or halocarbyl-substituted organometalloid, or $R_3$ and $R_4$ are joined to form a ring structure;

$T_1$ and $T_2$ are each independently C, N, or P;

$T_3$ and $T_4$ are each independently C, N, P or Si, except that where E is S, $T_3$ and $T_4$ are both C;

$T_5$ and $T_6$ are each independently C, N, or P;

n is 2, 3 or 4, depending on the oxidation number of M and the valency or valencies of each group X;

each group X is independently selected from among halogen, alkoxide, aryloxide, amide, phosphide, hydride, hydrocarbyl, substituted hydrocarbyl, halocarbyl, substituted halocarbyl, hydrocarbyl-substituted organometalloid, or halocarbyl-substituted organometalloid, or two X groups are joined to form a ring structure;

---- is a single or double bond; and each J is independently a $CH_2$ group (as in Compound 5, below) or a covalent bond (i.e., directly bonding one of the depicted S atoms with either $T_1$ or $T_2$, as in Compounds 1 and 4, below).

In addition, the present invention is directed to ligand compounds which can readily be reacted to provide a catalyst precursor of the present invention as defined above, such ligand compounds including compounds having a formula selected from among:

Formula 3

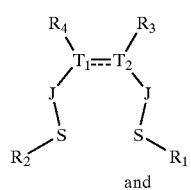

and

Formula 4

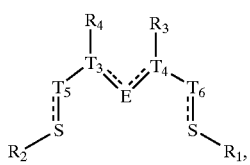

wherein E, $R_1$, $R_2$, $R_3$, $R_4$, $T_1$, $T_2$, $T_3$, $T_4$ and ---- have the same definitions as set forth above.

In formulas 1–4 above, preferred groups for $R_1$ and/or $R_2$ include 2,4,6-triisopropylphenyl and 2,4,6-trimethylphenyl.

In formulas 1 and 3 above, $R_3$ and $R_4$ are preferably joined so as to form, together with $T_1$ and $T_2$, a six-membered ring, most preferably a phenyl group.

In formulas 2 and 4 above, $R_3$ and $R_4$ are preferably joined so as to form, together with $T_1$, E and $T_2$, a six-membered ring, most preferably a pyridyl group.

In formulas 2 and 4 above, E is preferably O or N.

In formulas 1–4 above, M is preferably selected from among Ni, Pd, Co, Fe, Pt, Rh, Ir, Ru and Os. Most preferably, M is either Ni or Pd.

In formulas 1–4 above, the or each X is preferably halogen, or alkyl, most preferably Cl or methyl.

The present invention also provides a method of forming a catalyst precursor compound as defined above, in which a ligand compound as defined above is employed as a reactant.

The present invention also provides a catalyst composition comprising a catalyst precursor compound according to the present invention and an activating co-catalyst, as disclosed below.

The present invention also provides a catalyst system comprising a catalyst precursor according to the present invention and an activating co-catalyst, in which the catalyst precursor and the activating co-catalyst are introduced to a reaction system at different locations.

The present invention further provides a process for producing an olefin polymer, which comprises contacting at least one olefin monomer under polymerization conditions with a catalyst precursor compound, a catalyst composition and/or a catalyst system as described above. As described below, a wide variety of olefin polymers can be produced according to the present invention, with a preferred olefin polymer being polyethylene, preferably of relatively high molecular weight, typically in the range of from 10,000 to 10,000,000, although the present invention is not limited to any particular molecular weight.

The present invention further provides olefin polymers, such as ethylene polymers, produced by a process as described in the preceding paragraph, and products, e.g., blown and cast films including clarity and shrink applications, extrusion coatings, wire and cable insulation and jacketing, crosslinked power cable insulation, molded articles made by injection molding, blow molding or rotational molding, extrusions of pipe, tubing, profiles and sheeting, and insulating and semiconductive jacketing and/or shields, etc., made from such olefin polymers.

DETAILED DESCRIPTION OF THE INVENTION

In this specification, the term "olefinically unsaturated hydrocarbons" is often represented for convenience by "olefins".

The expression "copolymer" (and other terms incorporating this root), as used herein, refers to polymers containing two or more comonomers, i.e, it encompasses copolymers, terpolymers, etc.

As mentioned above, the catalyst precursor of the present invention has one of the following formulas:

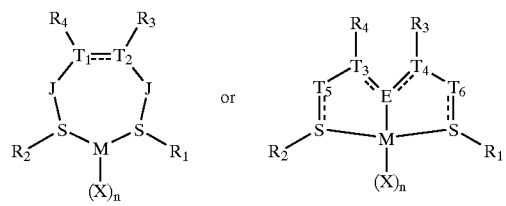

While the present invention is not limited to any particular theoretical mechanisms of action, it is believed, based on structural characterization (e.g., of 1,2-bis(2,4,6, triisopropylthiophenol)ethane palladium dichloride), that at least some of the transition metal/ligand complexes according to the present invention contain the ligand bound to the transition metal in a $0^2$ fashion, giving a square planar complex with $C_2$ symmetry.

As mentioned above, particularly preferred transition metals in accordance with the present invention include Ni and Pd. Bisthioether Ni and Pd complexes according to the present invention are especially preferred catalysts for the polymerization of olefins, providing good activity in such reactions. The lower electrophilicity of Ni and Pd (e.g., as compared to that of Ti and Zr) offers the enhanced possibility of polar comonomer incorporation into growing polymer chains. In addition, it has been found that the catalysts of the present invention, in particular Ni and Pd complexes, surprisingly can provide acceptable polymer production with the use of activators other than MMAO and MAO (MMAO and MAO are relatively expensive), and that such catalysts can instead be effectively activated with co-catalysts such as TEAl and TiBA.

Listed below are several representative examples of preferred catalyst precursor compounds according to the present invention:

Compound 1: 1,2-bis(2,4,6, triisopropylthiophenol)ethane palladium dihalide;

Compound 2: pyridine-2,6-((2,4,6-triisopropylthiophenol) methyl)$_2$ palladium dihalide;

Compound 3: bis(1-ethyl(2,4,6-triisopropylthiophenol)) ether palladium dihalide;

Compound 4: 1,2-(bis(2,4,6-triisopropylthiophenol)) benzene palladium dihalide; and Compound 5: 1,2-(bis(2,4,6-triisopropylthiophenol)methyl) benzene palladium dihalide.

Each of Compounds 1–5 is depicted below:

Compound 1
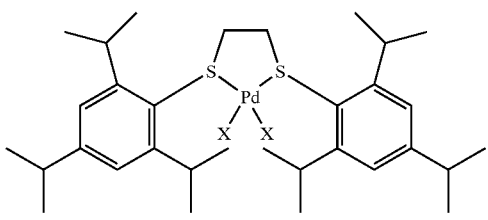

Compound 2
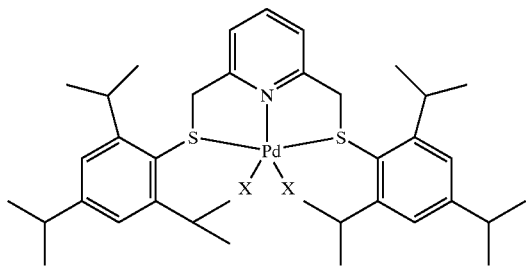

Compound 3
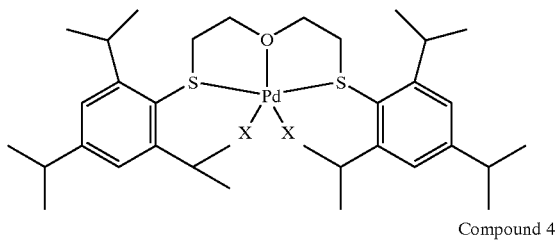

Compound 4
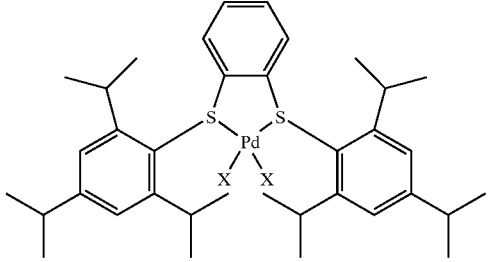

Compound 5
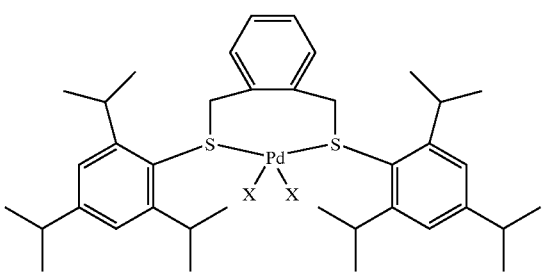

where X is a halogen.

Listed below are corresponding preferred ligand compounds:

Compound 6: 1,2-bis(2,4,6, triisopropylthiophenol)ethane;
Compound 7: pyridine-2,6-((2,4,6-triisopropylthiophenol)methyl)$_2$;
Compound 8: bis(1-ethyl(2,4,6-triisopropylthiophenol))ether;
Compound 9: 1,2-(bis(2,4,6-triisopropylthiophenol))benzene; and
Compound 10: 1,2-(bis(2,4,6-triisopropylthiophenol)methyl)benzene.

The ligand compounds according to the present invention may be prepared by any suitable synthesis method, and those of skill in the art would readily be able to prepare any of the compounds within the scope of the present invention. For example, in a suitable method for providing 1,2-bis(2,4,6-triisopropylthiophenol)ethane, the sterically demanding aromatic thiol, 2,4,6-triisopropylthiophenol may be synthesized by reducing 2,4,6-triisopropylphenyl sulphonyl chloride, followed by reacting a salt (e.g., a Li salt can be prepared by reacting free thiol with n-butyl lithium at low temperature in alkanes) of the resulting 2,4,6-triisopropylthiophenol with 1,2-dibromoethane, in the presence of a suitable reaction medium, for example, sodium hydroxide and ethanol. Similarly, pyridine-2,6-((2,4,6-triisopropylthiophenol)methyl)$_2$ can be prepared by reacting lithium-(2,4,6-triisopropylthiophenol), obtained as described above, with 2,6-bis(bromomethyl)pyridine; bis(1-ethyl(2,4,6-triisopropylthiophenol))ether can be prepared by reacting lithium-(2,4,6-triisopropylthiophenol) with bis(bromoethyl)ether, and 1,2-(bis(2,4,6-triisopropylthiophenol)methyl)benzene can be prepared by reacting lithium-(2,4,6-triisopropylthiophenol) with 1,2-bis(bromomethyl)benzene. Where, for example, a compound having one or two 2,4,6-trimethylthiophenol groups is desired, it may be obtained by employing 2,4,6-trimethylphenyl sulphonyl chloride in place of 2,4,6-triisopropylphenyl sulphonyl chloride.

Similarly, the catalyst precursor compounds of the present invention may be prepared by any suitable synthesis method, and those of skill in the art would readily be able to prepare them. For example, in a suitable method for preparing a Pd catalyst precursor compound, one of the ligands according to the present invention, e.g., one of those described in the preceding paragraph, may be reacted with $PdCl_2(C_6H_5CN)_2$.

The activating co-catalyst is capable of activating the catalyst precursor. A wide variety of activating co-catalysts are known in the art, any of which could be used in accordance with the present invention.

Preferred examples of suitable co-catalysts include linear or cyclic (co)oligomeric compounds having a formula selected from among (a), (b) and (c) set forth below in this paragraph: (a) $(M_{co-cat}R_5O)_n$, where $R_5$ is hydrogen or a $C_1$–$C_8$ hydrocarbyl group, preferably methyl, ethyl or aryl (e.g., substituted or unsubstituted phenyl or naphthyl), and n is an integer (see U.S. Pat. No. 5,527,752, col. 6, line 19–col. 7, line 4 for a discussion of this type of co-catalyst, and suitable methods for their production), (b) $(M_{co-cat}R_6O)_p (M_{co-cat}R_7O)_q$, wherein $M_{co-cat}$ is a metal selected from among alkali metals, alkali earth metals, rare earth metals, aluminum and tin, aluminum being preferred, $R_6$ and $R_7$ are each independently selected from among hydrogen and $C_1$–$C_8$ hydrocarbyl groups, and p and q are each independently an integer from 1 to 100; and (c) $M_{co-cat}R_8$, $M_{co-cat}R_8R_9$, $M_{co-cat}R_8R_9R_{10}$, or $M_{co-cat}R_8R_9R_{10}R_{11}$, wherein $M_{co-cat}$ is a metal selected from among alkali metals, alkali earth metals, rare earth metals, aluminum and tin, aluminum being preferred, and $R_8$, $R_9$, $R_{10}$ and $R_{11}$, where present, are each independently selected from among hydrogen, $C_1$–$C_8$ hydrocarbyl groups and $C_1$–$C_8$ alkoxy groups. Specific preferred examples of such co-catalysts include MAO, MMAO, triethyl aluminum (TEAl) and triisobutyl aluminum (TIBA). Especially preferred is the use of MMAO co-catalyst in the absence of hydrogen. However, as noted above, surprisingly, the catalyst of the present invention can provide acceptable results without the use of more expensive co-catalysts such as methyl alumoxane (MAO) or modified methyl alumoxane (MMAO), e.g., by instead using TEAl or TIBA co-catalysts. Other specific suitable co-catalysts include compounds such as alkali metal alkyls, e.g., $LiR_8$, alkali earth metal alkyls, e.g., $MgR_8R_9$, as well as other metal alkyls, e.g., $ZnR_8R_9$, $SnR_8R_9R_{10}R_{11}$, and aluminum alkyls.

Further examples of co-catalysts which can be used according to the present invention include (Lewis acid) non-coordinating anions. These non-coordinating anion activators are optional, and are most preferably employed in addition to a co-catalyst as described in the preceding paragraph. Examples of suitable non-coordinating anion activators include compounds where boron is the anion, e.g., compounds of the formula $B(Ar_1\ Ar_2\ Ar_3)$, wherein B is boron in a valence state of 3; $Ar_1$, $Ar_2$, and $Ar_3$ are independently selected from among optionally substituted $C_6$–$C_{20}$ aromatic hydrocarbon radicals. Suitable aromatic hydrocarbon radicals include, but are not limited to, phenyl, naphthyl and anthracenyl radicals. These radicals may be unsubstituted or substituted one or more times with one or more substituents. Suitable substituents include, but are not limited to, hydrocarbyl radicals, organometalloid radicals, alkoxy and aryloxy radicals, alkylamido radicals, fluorine, fluorocarbyl radicals and fluorohydrocarbyl radicals. Such substituent(s) may be at any possible position(s) on the aromatic hydrocarbon radical(s), e.g., ortho, meta or para relative to the carbon atom bonded to the anion. One example of such a compound is $B(C_6F_5)_3$. U.S. Pat. No. 5,599,761 discloses some examples of non-coordinating anion compounds which are suitable for use as co-catalysts according to the present invention.

Additional examples of suitable non-coordinating anion activators include compounds having the formula [L—H]+ [$BAr_1Ar_2Ar_3Ar_4$]—, wherein:

[L—H]+ is a Bronsted acid, H being a hydrogen atom;

B is boron in a valence state of 3; and $Ar_1$, $Ar_2$, $Ar_3$ and $Ar_4$, are independently selected from among optionally substituted $C_6$–$C_{20}$ aromatic hydrocarbon radicals. Suitable aromatic hydrocarbon radicals include, but are not limited to, phenyl, naphthyl and anthracenyl radicals. These radicals may be unsubstituted or substituted one or more times with one or more substituents. Suitable substituents include, but are not limited to, hydrocarbyl radicals, organometalloid radicals, alkoxy and aryloxy radicals, alkylamido radicals, fluorine, fluorocarbyl radicals and fluorohydrocarbyl radicals. Such substituent(s) may be at any possible position(s) on the aromatic hydrocarbon radical(s), e.g., ortho, meta or para relative to the carbon atom bonded to the anion.

In a preferred aspect of the invention, the activating cocatalyst is one of the following: a) a branched or cyclic oligomeric poly(hydrocarbylaluminum oxide)s which contains repeating units of the general formula —(Al(R*)O)—, where R* is a hydrogen, an alkyl radical containing from 1 to about 12 carbon atoms, or an aryl radical such as a substituted or unsubstituted phenyl or napthyl group; b) ionic salts of the general formula [A+][BR$_4$–], where A+ is a cationic Lewis or Bronsted acid capable of abstracting an alkyl, halogen, or hydrogen from catalysts, B is boron, and R is a substituted aromatic hydrocarbon, preferably a perfluorphenyl radical; c) boron alkyls of the general formula BR$_3$, where R is as defined above; or mixtures thereof. The activating cocatalyst may also be an organoaluminum compound, such as triisobutylaluminum or diethylaluminum chloride.

In a further preferred aspect of the present invention, a combination of at least one Lewis acid and at least one alumoxane is used.

Co-catalysts as described above are known in the art, and can be prepared by those of ordinary skill in the art using any of a variety of known techniques. For instance, alumoxanes may be prepared in any of a variety of ways. According to one method of preparing alumoxanes, a mixture of linear and cyclic alumoxanes is obtained in the preparation of alumoxanes from, for example, trimethylaluminum and water. For example, an aluminum alkyl may be treated with water in the form of a moist solvent. Alternatively, an aluminum alkyl, such as trimethylaluminum, may be contacted with a hydrated salt, such as hydrated ferrous sulfate. The latter method comprises treating a dilute solution of trimethylaluminum in, for example, toluene with a suspension of ferrous sulfate heptahydrate. It is also possible to form methylalumoxanes by the reaction of a tetraalkyldialumoxane containing $C_2$ or higher alkyl groups with an amount of trimethylaluminum that is less than a stoichiometric excess. The synthesis of methylalumoxanes may also be achieved by the reaction of a trialkyl aluminum compound or a tetraalkyldialumoxane containing $C_2$ or higher alkyl groups with water to form a polyalkyl alumoxane, which is then reacted with trimethylaluminum. Further modified methylalumoxanes, which contain both methyl groups and higher alkyl groups, i.e., isobutyl groups, may be synthesized by the reaction of a polyalkyl alumoxane containing $C_2$ or higher alkyl groups with trimethylaluminum and then with water as disclosed in, for example, U.S. Pat. No. 5,041,584.

The amount of catalyst usefully employed in the catalyst composition may vary within a wide range. It is generally preferred to use the catalyst compositions at concentrations sufficient to provide at least about 0.000001, preferably about 0.00001 percent, by weight, of transition metal based on the weight of the monomers. The upper limit of the percentages is determined by a combination of catalyst activity and process economics. When the activating cocatalyst is a branched or cyclic oligomeric poly (hydrocarbylaluminum oxide), the mole ratio of aluminum atoms contained in the poly(hydrocarbylaluminum oxide) compound to total metal atoms contained in the catalyst precursor is generally in the range of from about 2:1 to about 100,000:1, preferably in the range of from about 10:1 to about 10,000:1, and most preferably in the range of from about 50:1 to about 2,000:1. When the activating co-catalyst is of the formula $(AlR_{15}O)_p\ (AlR_{16}O)_q$, the mole ratio of aluminum atoms contained in the $(AlR_{15}O)_p\ (AlR_{16}O)_q$ compound to total metal atoms contained in the catalyst precursor is generally in the range of from about 1:1 to about 100,000:1, preferably in the range of from about 5:1 to about 2000:1, and most preferably in the range of from about 10:1 to about 500:1. Likewise, suitable amounts of non-coordinating anion type co-catalysts can vary widely according to information known in the art, and based on routine evaluation by those skilled in the art. According to the present invention, non-coordinating anion co-catalysts may be used in combination with alumoxane co-catalysts, and in such circumstances, there is no minimum amount of non-coordinating anion required.

The catalyst composition may optionally contain one or more other polyolefin catalysts. These catalysts include, for example, any Ziegler-Natta catalysts containing a metal from groups IV(B), V(B), or VI(B) of the Periodic Table. Suitable activators for Ziegler-Natta catalysts are well known in the art and may also be included in the catalyst composition.

The catalyst precursor and the activating co-catalyst may be independently or simultaneously (a) impregnated onto a solid support, (b) in liquid form such as a solution or dispersion, (c) spray dried with a support material, (d) in the form of a prepolymer, or (e) formed in the reactor in-situ during polymerization.

For example, in one suitable aspect, the support may first be impregnated with a hydrocarbon solution of the co-catalyst, dried of solvent followed by reimpregnation with the metal catalyst solution followed by solvent removal. Alternatively, the base support may be impregnated with the reaction product of the metal catalyst precursor and the co-catalyst followed by removal of the solvent. In either case, a hydrocarbon slurry of the supported, activated catalyst or a hydrocarbon-free powder results and these are used, usually without added activator as olefin polymerization catalysts. Frequently, an impurity scavenger is added to the reaction prior to or along with the catalyst-cocatalyst slurry/powder in order to maximize its activity. Alternatively, the support can first be heated to drive off hydroxylic impurities notably water followed by reaction of the remaining hydroxyl groups with proton scavengers such as hydrocarbyl aluminum compounds (TMA, TEA, TIBAL, TNHAL, MAO, MMAO, etc.). Also, the heating may be omitted and the support reacted directly with the hydrocarbyl aluminum compounds. In another preferred aspect, the catalyst precursor is dissolved in a solvent, a cocatalyst is then added to the dissolved catalyst precursor, and the resulting product is introduced into a reactor via a feeding line. Another preferred aspect involves mixing the catalyst precursor with a cocatalyst solution in a solvent (e.g., an organic solvent such as toluene), adding a support material (e.g., silica), removing solvent (e.g., by drying in a vacuum and heating), and introducing the resulting product into a reactor via a feeding line either as a solid feed or slurry (created, e.g., by mixing the product in a liquid, e.g., hexane), preferably in, e.g., mineral oil, such as Kaydol oil.

In the case of impregnation on a support, the activating co-catalyst and/or catalyst precursor may be impregnated in or deposited on the surface of an inert substrate such as silicon dioxide (silica), aluminum oxide (alumina), carbon black, polyethylene, polycarbonate, polystyrene, zinc oxide, polypropylene, thoria, zirconia, or magnesium halide (e.g., magnesium dichloride), and mixtures thereof, such that the catalyst composition is between 0.1 and 90 percent by weight of the total weight of the catalyst composition and the support. These supports preferably have been calcined at a temperature sufficient to remove substantially all physically bound water. Conventional techniques, such as those disclosed in U.S. Pat. No. 4,521,723, can be employed for impregnating the activating co-catalyst and/or catalyst precursor onto a catalyst support.

A preferred support material is a silica material. For example, some such materials are described in U.S. Pat. No. 5,264,506. Desirably, the silica support has an average particle size of from about 60 to 200 (preferably about 70 to 140) microns; preferably, no more than about 30 percent by weight silica should have a particle size below about 44 microns. Further, the silica support has an average pore diameter of greater than about 100 Angstrom units, preferably greater than about 150 Angstrom units. It is also desirable for the silica support to have a surface area greater than about 200 square meters per gram. The support is preferably substantially dry, that is, free of adsorbed water. Drying of the silica may be carried out by heating it at a temperature of from about 100 to 800 degrees C., e.g., about 600 degrees C.

Suitable liquid form catalyst compositions are described, e.g., in U.S. Pat. No. 5,317,036. Unsupported liquid form catalyst compositions, i.e., which include liquid catalyst precursor, liquid co-catalyst, solution(s) or dispersion(s) thereof in the same or different solvent(s), and combinations thereof, can have a number of practical benefits. Unsupported catalyst compositions avoid the costs associated with support material and its preparation, and can provide for the realization of a very high catalyst surface area to volume ratio. Furthermore, unsupported catalyst compositions produce polymers which usually have a much lower residual ash content then polymers produced using supported catalyst compositions.

Spray-drying may be effected by any spray-drying method known in the art. Spray-drying can be useful to provide catalysts having a narrow droplet size distribution (and resulting narrow particle size distribution) for efficient use of the catalyst and to give more uniform pellets and better performance, in addition to having beneficial morphology.

For example, one example of a suitable spray-drying method comprises atomizing a solution, suspension or dispersion of the catalyst and/or the activating co-catalyst, optionally together with a filler, and optionally with heating of the solution, suspension or dispersion. Atomization is accomplished by means of any suitable atomizing device to form discrete spherically shaped particles. Atomization is preferably effected by passing the slurry through the atomizer together with an inert drying gas, i.e., a gas which is nonreactive under the conditions employed during atomization. An atomizing nozzle or a centrifugal high speed disc can be employed to effect atomization, whereby there is created a spray or dispersion of droplets of the mixture. The volumetric flow of drying gas, if used, preferably considerably exceeds the volumetric flow of the slurry to effect atomization of the slurry and/or evaporation of the liquid medium. Ordinarily the drying gas is heated to a temperature as high as about 160 degrees C. to facilitate atomization of the slurry; however, if the volumetric flow of drying gas is maintained at a very high level, it is possible to employ lower temperatures. Atomization pressures of from about 1 psig to 200 psig are suitable. Some examples of suitable spray-drying methods include those disclosed in U.S. Pat. Nos. 5,290,745, 5,652,314, 4,376,062, 4,728,705, 5,604,172, 5,306,350 and 4,638,029.

Another type of suitable spray-drying method comprises forming a liquid mixture comprising a nonvolatile materials fraction, a solvent fraction and at least one compressed fluid; and spraying the liquid mixture at a temperature and pressure that gives a substantially decompressive spray by passing the mixture through an orifice into an environment suitable for forming solid particulates by solvent evaporation. For example, such a method is disclosed in U.S. Pat. No. 5,716,558.

In general, spray-drying produces discrete, substantially round, abrasive resistant particles with relatively narrow particle size distribution. By adjusting the size of the orifices of the atomizer employed during spray drying, it is possible to obtain particles having desired average particle size, e.g., from about 5 micrometers to about 200 micrometers. The particles recovered from the spray drying step can optionally be decarboxylated by heating the particles, e.g., as disclosed in U.S. Patent No. 5,652,314.

As mentioned above, catalyst precursor and/or activating co-catalyst may be in the form of a prepolymer. Such prepolymers can be formed in any suitable manner, e.g., by forming one or more polymer or copolymer (which may be the same or different from the polymer(s) and/or copolymer(s) to be collected in the reactor) in the presence of the catalyst precursor and/or activating co-catalyst. For example, processes which provide catalyst precursor and/or activating co-catalyst attached to and at least partially covered by polymeric and/or copolymeric material may be suitable.

The catalyst system may optionally be treated with an amine activator. By adding an amine to the catalyst precursor and then subsequently adding the cocatalyst, some catalyst systems yield higher activities than when no amine pretreatment occurs or when the amine treatment is added to the catalyst system containing both the precursor and cocatalyst. Indeed, this latter treatment has even yielded an inhibited catalyst system from an activity perspective. The level of amine addition ranges from 0.1 to 10 moles of amine per mole of transition metal, preferably from 1 to 5 moles amine per mole of transition metal. Suitable amines include, but are not limited to, ethyl amine, diethyl amine, triethyl amine, piperidine and the like.

The catalyst composition may be used for the polymerization of olefins by any suspension, solution, slurry, or gas phase process, using known equipment and reaction conditions, and is not limited to any specific type of reaction system. Such polymerization can be conducted in a batch-wise mode, a continuous mode, or any combination thereof. Generally, suitable olefin polymerization temperatures are in the range of from about 0 degrees C. to about 200 degrees C. at atmospheric, subatmospheric, or superatmospheric pressures.

Preferably, gas phase polymerization is employed, at superatmospheric pressure in the range of from about 1 to about 1000 psi, preferably 50 to 400 psi, most preferably 100 to 300 psi, and at temperatures in the range of from about 30 degrees C. to about 130 degrees C., preferably about 65 degrees C. to about 110 degrees C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions sufficient to polymerize the monomer(s) and in the presence of an effective amount of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,543,399, 4,588,790, 5,352,749 and 5,462,999, and recycled to the reactor. Product is withdrawn from the reactor and make-up monomer is added to the recycle stream. In addition, a fluidization aid such as carbon black, silica, clay, or talc may be used, as disclosed in U.S. Pat. No. 4,994,534. Suitable gas phase reaction systems are also described in U.S. Pat. No. 5,527,752.

Slurry or solution polymerization processes may utilize subatmospheric or superatmospheric pressures and temperatures in the range of from about 40 degrees C. to about 110 degrees C. Useful liquid phase polymerization reaction systems are known in the art, e.g., as described in U.S. Pat. Nos. 3,324,095, 5,453,471, 5,527,752, 5,834,571, WO 96/04322 (PCT/US95/09826) and WO 96/04323 (PCT/US95/09827). Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. Preferably, reaction medium containing the olefin polymer product and unreacted olefin monomer is withdrawn continuously from the reactor. Olefin polymer product is separated, and unreacted olefin monomer is recycled into the reactor.

Polymerization may be carried out in a single reactor or in two or more reactors in series. Where tandem reactors are employed (i.e., two or more reactors in series), the reactors may each have a unique set of reaction conditions, i.e., one or more reaction condition is different in one reactor relative to one or more other reactor. The use of different conditions in different reactors, can be useful where a broadening of the product molecular weight distribution is desired.

Polymerization is preferably conducted substantially in the absence of undesirable catalyst poisons, such as moisture, oxygen, carbon monoxide, carbon dioxide, acetylene, and the like. Organometallic compounds may be employed as scavenging agents for removal of poisons, when necessary, to increase catalyst activity. Examples of scavenging agents include metal alkyls, preferably aluminum alkyls, most preferably triisobutylaluminum or tri-n-hexyl aluminum. As noted above, however, the present invention provides catalyst precursor compounds and catalyst compositions which have good resistance to such catalyst poisons.

Conventional adjuvants may be included in the process, provided they do not interfere with the operation of the catalyst composition in forming the desired polyolefin. If desired, hydrogen or a metal or non-metal hydride, e.g., a silyl hydride, may be used as a chain transfer agent in the process. Where desired, hydrogen may be used preferably in amounts up to about 10 moles of hydrogen per mole of total monomer feed, although as mentioned above, it is preferred that the reactants and the catalyst of the present invention be free of or substantially free of hydrogen.

As desired for temperature control of the system, any gas inert to the catalyst composition and reactants may also be present in the gas stream.

Other conventional additives may be included in the process, provided they do not interfere with the operation of the catalyst composition in forming the desired polyolefin. For example, other additives which may be introduced into one or more streams entering polymer formulation include antioxidants, coupling agents, ultraviolet absorbers or stabilizers, themo- or photo-oxidation stabilizers including hindered phenolic and hydroxy amino antioxidants, hindered amine light stabilizers, thioesters, disulfide phosphites, aryl phosphites, or phosphonites, colorants (e.g., carbon blacks and titanium dioxide), antistatic agents, pigments, dyes, nucleating agents, reinforcing fillers or polymer additives, slip agents, plasticizers, processing aids (e.g., fluoroelastomers), lubricants (e.g., metallic stearates), slip agents (e.g., oleamide or erucamide), viscosity control agents, tackifiers, antiblock or release agents (e.g., stearamide, ethylene bis-stearamide, controlled particle size zeolite, calcium carbonate, talc or silica), blowing agents, surfactants, extenders oils, metal deactivators, voltage stabilizers, flame retardants, crosslinking agents, boosters, catalysts, Lewis bases (see U.S. Pat. No. 5,527,752) and smoke suppressants. Fillers and additives can be added in amounts ranging from less than about 0.1 to more than about 200 parts by weight for each 100 parts by weight of the base resin, for example, polyethylene.

Examples of antioxidants are: hindered phenols such as tetrakis [methylene(3,5-di-tert-butyl-4-hydroxyhydrocinnamate)]methane, bis[(beta-(3,5-di-tert-butyl-4-hydroxybenzyl)-methyl-carboxyethyl)]sulphide, 4,4'-thiobis(2-methyl-6-tert-butylphenol), 4,4'-thio-bis(2-tert-butyl-5-methyl-phenol), 2,2'-thiobis(4-methyl-6-tert-butylphenol), and thiodiethylene bis(3,5-di-tert-butyl-4-hydroxy)hydrocinnamate; phosphites and phosphonites such as tris(2,4-di-tert-butylphenyl) phosphite and di-tert-butylphenyl-phosphonite; thio compounds such as dilaurylthiodipropionate, dimyristylthiodipropionate, and distearylthiodipropionate; various siloxanes; and various amines such as polymerized 2,2,4-trimethyl-1,2-dihydroquinoline. Antioxidants can be used in amounts of about 0.1 to about 5 parts by weight per 100 parts by weight of polyethylene.

Olefin polymers and copolymers that may be produced according to the invention include, but are not limited to, ethylene homopolymers, homopolymers of linear or branched higher alpha-olefins containing 3 to about 20 carbon atoms, and copolymers of olefin (preferably ethylene) and (a) higher alpha-olefins, (b) cyclic olefins or (c) alpha olefin-dienes. Suitable higher alpha-olefins include, for example, propylene, 1-butene, 1-pentene, 1-hexene, 4-methyl-1-pentene, 1-octene, and 3,5,5-trimethyl-1-hexene. Suitable cyclic olefins include, for example, norbornene and styrene. Suitable alpha olefin-dienes include linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like. Other suitable monomers include olefins having one or more strained double bonds such as bicyclo (2.2.1) hepta-2,5-diene, 5-ethylidine-2-norbornene, 5-vinyl-2-norborene (endo and exo forms or mixtures thereof) and normal mono-olefins.

Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well.

Specific olefin polymers that may be made according to the invention include, for example, polyethylene, higher olefins, e.g., polypropylene, ethylene/higher olefin, e.g., propylene copolymers (e.g., EPR's), ethylene/higher olefin, e.g. propylene/diene terpolymers (e.g., EPDM's), ethylene/higher olefin, e.g., propylene/cyclic olefin terpolymers, polybutadiene, polyisoprene and the like.

As mentioned above, the present invention offers the possibility of incorporating polar comonomer into growing polymer chains.

Polymers produced by methods according to the present invention can be crosslinked by adding a crosslinking agent to the composition or by making the resin hydrolyzable, by adding hydrolyzable group. Suitable cross-linking agents are organic peroxides such as dicumyl peroxide; 2,5-dimethyl-2,5-di(t-butylperoxy)hexane; t-butyl cumyl peroxide; and 2,5-dimethyl-2,5-di(t-butylperoxy)hexane-3. Dicumyl peroxide is preferred. Hydrolyzable groups can be added to polymers produced by methods according to the present invention, for example, by copolymerizing ethylene with an ethylenically unsaturated compound having one or more—$Si(OR)_3$ groups such as vinyltrimethoxy-silane, vinyltriethoxysilane, and gamma-methacryloxypropyltrimethoxysilane or grafting these silane compounds to the resin in the presence of the aforementioned organic peroxides. The hydrolyzable resins are then crosslinked by moisture in the presence of a silanol condensation catalyst such as dibutyltin dilaurate, dioctyltin maleate, dibutyltin diacetate, stannous acetate, lead naphthenate, and zinc caprylate. Dibutyltin dilaurate is preferred.

Examples of hydrolyzable copolymers and hydrolyzable grafted copolymers are ethylene/vinyltrimethoxy silane copolymer, ethylene/gamma-methacryloxypropyltrimethoxy silane copolymer, vinyltrimethoxy silane grafted ethylene/ethyl acrylate copolymer, vinyltrimethoxy silane grafted linear low density ethylene/1-butene copolymer, and vinyltrimethoxy silane grafted low density polyethylene.

As indicated above, the present invention is further directed to blown and cast films including clarity and shrink applications, extrusion coatings, wire and cable insulation and jacketing, crosslinked power cable insulation, molded articles made by injection molding, blow molding or rotational molding, extrusions of pipe, tubing, profiles and sheeting, and insulating and semiconductive jacketing and/or shields, etc., made from olefin polymers produced using the catalyst precursors, catalyst compositions and/or catalyst systems described above. Methods of making these and other products are well known in the art.

EXAMPLES

The following examples further illustrate the invention.

Example 1

Synthesis of 1,2-bis(2,4,6, triisopropylthiophenol) ethane)

A round bottom flask was charged with 1,2-dibromoethane (9.75 mmol; 0.84 mL), 2,4,6-triisopropylthiophenol (19.5 mmol; 4.60 g), sodium hydroxide (19.5 mmol; 4.60 g) and ethanol (100 mL). After stirring for 3 hours at room temperature, a white solid precipitated from solution. Removal of the volatiles gave a pale yellow solid which was extracted with hexane and then pumped down to dryness. Ethanol (2 mL) was added, giving a white flocculent material, which was collected onto a fritted funnel, and dried in vacuo. Yield: 2.36 g, 50%.

Example 2

Synthesis of pyridine-2,6-((2,4,6-triisopropylthiophenol)methyl)$_2$

To a solution of 2,6-bis(bromomethyl)pyridine (5 mmol; 1.325 g) in $Et_2O$ (40 mL) was added a solution of lithium-(2,4,6-triisopropylthiophenol) (10 mmol; 2.42 g) in $Et_2O$ (40 mL). The reaction was allowed to stir overnight at room temperature. The colorless solution was evaporated to dryness, extracted with 200 mL hexane and filtered through Celite. Removal of the volatiles gave fluffy colorless crystals, which were collected onto a fritted disk and dried in vacuo. Yield: 2.2 g, 71%.

Example 3

Synthesis of 1,2-bis(2,4,6, triisopropylthiophenol) ethane palladium dichloride [Compound 1. where X=Cl]

$PdCl_2(C_6H_5CN)_2$ (3 mmol; 1.15 g) was added as a solid to a solution of 1,2-bis(2,4,6, triisopropylthiophenol)ethane (3 mmol; 1.5 g) in 80 mL CH$_2$Cl$_2$. The reaction mixture was stirred over the weekend at room temperature and then filtered through Celite. After concentration of the solution to ca. 10 mL, 200 mL n-hexane was added causing the precipitation of an orange powder. The solids were collected onto a fritted disk, and dried in vacuo. Yield: 1.45 g; 71%. The complexes were recrystallized from the slow diffusion of hexane into a saturated methylene chloride solution containing the complex.

Example 4

Synthesis of trispentafluorophenyl boron activated 1.2-bis(2,4,6, triisopropylthiophenol)ethane palladium dichloride To a solution of 1,2-bis(2,4,6, triisopropylthiophenol) ethane palladium dichloride (0.25 mmol; 0.168 g) in a minimal volume of toluene (2 mL) was added a solution of B(C$_6$F$_5$)$_3$ (0.50 mmol; 0.206 g) in 1 mL toluene. The solution was stirred for one minute to dissolve the solids and then allowed to sit at room temperature overnight. The orange crystals were collected onto a fritted disk and dried in vacuo. Yield: 0.407 g; 100%.

Example 5

Polymerization Runs

Procedures similar to those described above in Examples 1–4 were employed to produce the catalyst materials set forth below for Runs 1–7.
Run Catalyst Composition
1 1,2-bis(2,4,6, triisopropylthiophenol)ethane palladium dichloride
2 1,2-bis(2,4,6, triisopropylthiophenol)ethane palladium dichloride/SiO$_2$/2 B(C$_6$F$_5$)$_3$
3 1,2-bis(2,4,6, triisopropylthiophenol)ethane palladium dichloride/2B(C$_6$F$_5$)$_3$
4 bis(1-ethyl(2,4,6-triisopropylthiophenol))ether palladium dichloride
5 1,2-bis(2,4,6, triisopropylthiophenol)ethane palladium dichloride/1B(C$_6$F$_5$)$_3$
6 1,2-bis(2,4,6, triisopropylthiophenol)ethane palladium dichloride/1B(C$_6$F$_5$)$_3$
7 1,2-(bis(2,4,6-triisopropylthiophenol)methyl)benzene palladium dichloride In each of Runs 1–7, a 1 liter stirred autoclave reactor was charged with 485 cc hexane, ca. 200–500 equivalents of MMAO to Pd, and sufficient catalyst oil slurry to give a charge of 9 µmoles of Pd. The reactor was pressurized with the desired volume of H$_2$, and the temperature was raised to 65 degrees C. (60 degrees C. in Run 3). Ethylene was fed to maintain a reactor pressure of 200 psig, and the temperature was controlled at 65 degrees C. (60 degrees C. in Run 3). After 30 minutes, ethylene feed was stopped, the reactor was cooled and vented, and granular high-density polyethylene was recovered. The results are shown in Table 1:

TABLE 1

| Run | Activity | Al:Pd Ratio | conditions | FI | MFR |
| --- | --- | --- | --- | --- | --- |
| 1 | 474 | 494:1 | 0 mL hexene | 5.9 | 16 |
| 2 | 5,443 | 1504:1 | 0 mL hexene | 8.8 | 15.5 |
| 3 | 1,293 | 164:1 | 0 mL hexene | — | — |
| 4 | 7,024 | 452:1 | 0 mL hexene | — | — |
| 5 | 2,860 | 271:1 | 50 mL hexene | 2.8 | 23 |
| 6 | 8,889 | 256:1 | 0 mL hexene | 7.3 | 17 |

TABLE 1-continued

| Run | Activity | Al:Pd Ratio | conditions | FI | MFR |
| --- | --- | --- | --- | --- | --- |
| 7 | 2,135 | 271:1 | 0 mL hexene | — | — | where:
activity is in units of g PE/mmol Pd A hr 100 psi C$_2$H$_4$;
density is in units of g/cm$^2$;
FI (flow index) was determined according to ASTM D-1238—Condition F; and
MFR (melt flow ratio) is the ratio of FI to melt index, melt index being determined according to ASTM D-1238—Condition E.

Run 8

A 1,2, bis(2,4,6, triisopropylthiophenol)ethane palladium dichloride/2B(C$_6$F$_5$)$_3$ catalyst composition, prepared following the general procedure as described in Examples 1, 3 and 4 above, was impregnated on a SiO$_2$ support. Polymerizations were done in a stirred gas phase reactor to prepare high molecular weight, high density polymer. MMAO was used as the co-catalyst, and the polymerization was carried out using an ethylene pressure of 200 psig at a temperature of 65 degrees C. The results were as follows:

| | |
| --- | --- |
| res. Pd: | 28 ppm |
| FI: | no flow |
| resin aps, in.: | 0.05 |
| bulk density: | 18 lb/ft$^3$ |
| Mn: | 0.508 × 10$^5$ |
| Mw: | 0.567 × 10$^6$ |
| PDI from SEC: | 11.2 |
| density: | 0.943 g/cm$^3$ | where:
"Res. Pd" is the amount (in ppm) of residual Pd contained in the product polymer, as measured by ICP (Inductively Coupled Plasma).

Flow Index was determined according to ASTM D-1238—Condition F.

"resin aps, in." is the average particle size (aps), in inches, of the product polymer, measured by sieving resin through fine meshes (10/18/35/60/120/200/pan) and averaging the size of the resin left on each of the screens.

Mw is the weight average molecular weight of the polymer;

Mn is the number average molecular weight of the polymer; and

PDI (polydispersity index) is defined as the ratio of the weight average molecular weight of the polymer to the number average molecular weight of the polymer (M$_w$/M$_n$).

Although the compounds, compositions, processes and products in accordance with the present invention have been described in connection with preferred embodiments, it will be appreciated by those skilled in the art that modifications not specifically described may be made without departing from the spirit and scope of the invention defined in the following claims.

Each of the U.S. Patents and PCT Publications identified above are hereby expressly incorporated by reference in their entireties.

What is claimed is:

1. A catalyst composition comprising:
(A) a catalyst compound having a formula selected from the group consisting of:

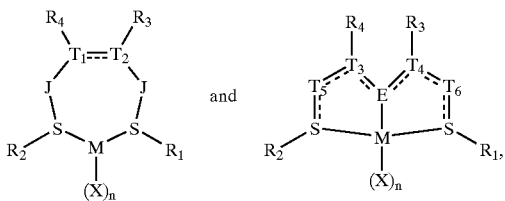

wherein:
E is O, S, N or P;
M is a transition metal;
$R_1$ and $R_2$ are each independently selected from among halogen, alkoxide, aryloxide, amide, phosphide, hydride, hydrocarbyl, substituted hydrocarbyl, halocarbyl, substituted halocarbyl, hydrocarbyl-substituted organometalloid, or halocarbyl-substituted organometalloid, or $R_1$ and $R_2$ are joined to form a ring structure;
$R_3$ and $R_4$ are each independently selected from the group consisting of hydrogen, halogen, alkoxide, aryloxide, amide, phosphide, hydride, hydrocarbyl, substituted hydrocarbyl, halocarbyl, substituted halocarbyl, hydrocarbyl-substituted organometalloid, and halocarbyl-substituted organometalloid, or $R_3$ and $R_4$ are joined to form a ring structure;
$T_1$ and $T_2$ are each independently C, N, or P;
$T_3$ and $T_4$ are each independently C, N, P or Si, except that where E is S, $T_3$ and $T_4$ are both C;
$T_5$ and $T_6$ are each independently C, N, or P;
n is 2, 3 or 4, depending on the oxidation number of M and the valency or valencies of each group X;
each group X is independently selected from the group consisting of halogen, alkoxide, aryloxide, amide, phosphide, hydride, hydrocarbyl, substituted hydrocarbyl, halocarbyl, substituted halocarbyl, hydrocarbyl-substituted organometalloid, and halocarbyl-substituted organometalloid, or two X groups are joined to form a ring structure;
---- is a single or double bond; and
each J is independently a $CH_2$ group or a covalent bond which directly bonds the depicted adjacent S atom with the depicted adjacent group $T_1$ or $T_2$, and
(B) an activating co-catalyst, a support material, or both an activating co-catalyst and a support material.
2. The catalyst composition of claim 1, wherein:
(a) the composition comprises a support material and said catalyst compound is impregnated on said support material; or
(b) said catalyst compound is dissolved or dispersed in a liquid.
3. The catalyst composition of claim 1 comprising an activating cocatalyst, wherein said activating co-catalyst has a formula selected from the group consisting of:
(a) $(M_{co-cat}R_5O)_n$, where $R_5$ is hydrogen or a $C_1$–$C_8$ hydrocarbyl group, and n in an integer,
(b) $(M_{co-cat}R_6O)_p (M_{co-cat}R_7O)_q$, wherein $M_{co-cat}$ is a metal selected from the group consisting of: alkali metals, alkali earth metals, rare earth metals, aluminum and tin; $R_6$ and $R_7$ are each independently selected from the group consisting of: hydrogen and $C_1$–$C_8$ hydrocarbyl groups, and p and q are each independently an integer from 1 to 100, and
(c) $M_{co-cat}R_8$, $M_{co-cat}R_8R_9$, $M_{co-cat}R_8R_9R_{10}$, or $M_{co-cat}R_8R_9R_{10}R_{11}$, wherein $M_{co-cat}$ is a metal selected from the group consisting of: alkali metals, alkali earth metals, rare earth metals, aluminum and tin, and $R_8$, $R_9$, $R_{10}$ and $R_{11}$, where present, are each independently selected from the group consisting of: hydrogen, $C_1$–$C_8$ hydrocarbyl groups an $C_1$–$C_8$ alkoxy groups.
4. A method of making a catalyst composition according to claim 1, comprising impregnating a catalyst compound on a support material or spray-drying a mixture comprising a catalyst compound and an activating co-catalyst; a catalyst compound and a support material; or a catalyst compound, an activating co-catalyst and a support material, said catalyst compound having a formula selected from the group consisting of:

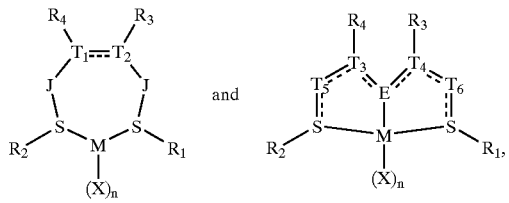

wherein:
E is O, S, N or P;
M is a transition metal;
$R_1$ and $R_2$ are each independently selected from the group consisting of halogen, alkoxide, aryloxide, amide, phosphide, hydride, hydrocarbyl, substituted hydrocarbyl, halocarbyl substituted halocarbyl, hydrocarbyl-substituted organometalloid, and halocarbyl-substituted organometalloid, or $R_1$ and $R_2$ are joined to form a ring structure;
$R_3$ and $R_4$ are each independently selected from the group consisting of hydrogen, halogen, alkoxide, aryloxide, amide, phosphide, hydride, hydrocarbyl, substituted hydrocarbyl, halocarbyl, substituted halocarbyl, hydrocarbyl-substituted organometalloid, and halocarbyl substituted organometalloid, or $R_3$ and $R_4$ are joined to form a ring structure;
$T_1$ and $T_2$ are each independently C, N, or P;
$T_3$ and $T_4$ are each independently C, N, P or Si, except that where E is S, $T_3$ and $T_4$ are both C;
$T_5$ and $T_6$ are each independently C, N, or P;
n is 2, 3 or 4, depending on the oxidation number of M and the valency or valencies of each group X;
each group X is independently selected from the group consisting of halogen, alkoxide, aryloxide, amide, phosphide, hydride, hydrocarbyl, substituted hydrocarbyl, halocarbyl, substituted halocarbyl, hydrocarbyl-substituted organometalloid, and halocarbyl-substituted organometalloid, or two X groups are joined to form a ring structure;
---- is a single or double bond; and
each J is independently a $CH_2$ group or a covalent bond which directly bonds the depicted adjacent S atom with the depicted adjacent group $T_1$ or $T_2$.
5. A catalyst composition according to claim 1 wherein M is Ni, Pd, Co, Fe, Pt, Rh, Ir, Ru, or Os.
6. A catalyst composition according to claim 1 wherein M is Ni, or Pd.

7. A catalyst composition according to claim 1 wherein X is halogen or alkyl.

8. A catalyst composition according to claim 1 wherein X is Cl, or methyl.

9. A catalyst composition according to claim 5 wherein X is halogen, or alkyl.

10. A catalyst composition according to claim 6 wherein X is Cl, or methyl.

11. A catalyst composition according to claim 1 wherein $R_1$ and $R_2$ are 2,4,6-triisopropylphenyl or 2,4,6-trimethylphenyl.

12. A catalyst composition according to claim 5 wherein $R_1$ and $R_2$ are 2,4,6-triisopropylphenyl or 2,4,6-trimethylphenyl.

13. A catalyst composition according to claim 6 wherein $R_1$ and $R_2$ are 2,4,6-triisopropylphenyl or 2,4,6-trimethylphenyl.

14. A catalyst composition according to claim 9 wherein $R_1$ and $R_2$ are 2,4,6-triisopropylphenyl or 2,4,6-trimethylphenyl.

15. A catalyst composition according to claim 14 wherein the catalyst compound is selected from the group consisting of:

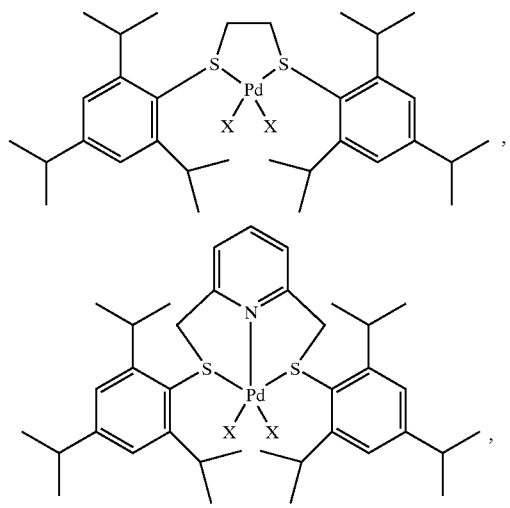

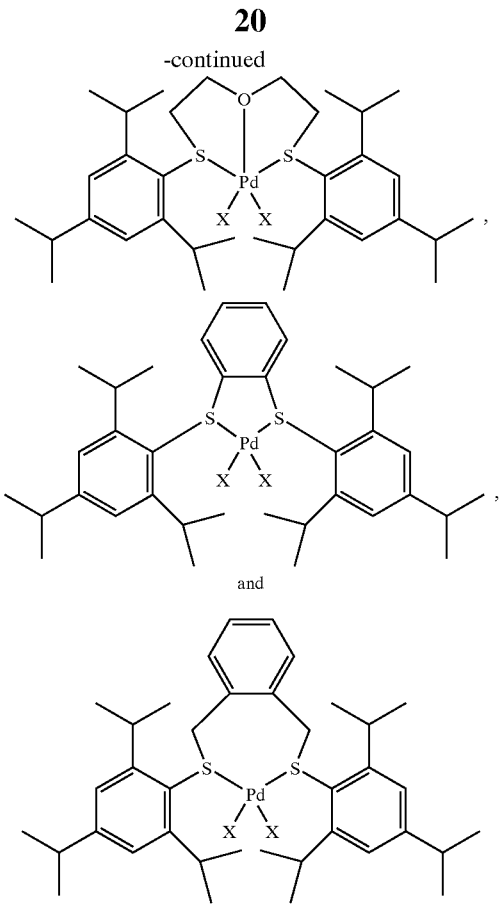

wherein each X is halogen.

16. A catalyst composition according to any one of claims 1–3, and 5–15 comprising an alumoxane cocatalyst.

* * * * *

UNITED STATES PATENT AND TRADEMARK OFFICE
CERTIFICATE OF CORRECTION

PATENT NO. : 6,511,934 B1
DATED : January 28, 2003
INVENTOR(S) : Jessica A. Cook and John J. Bielak It is certified that error appears in the above-identified patent and that said Letters Patent is hereby corrected as shown below:

Column 18,
Line 9, "an" should read -- and --.

Signed and Sealed this

Twenty-second Day of July, 2003

JAMES E. ROGAN
*Director of the United States Patent and Trademark Office*